United States Patent [19]

McKnight et al.

[11] Patent Number: 4,561,435
[45] Date of Patent: Dec. 31, 1985

[54] WOUND DRESSING

[75] Inventors: James T. McKnight, Pleasantville, N.Y.; Paul Silverstein, Oklahoma City, Okla.

[73] Assignee: Chesebrough-Ponds, Inc., Greenwich, Conn.

[21] Appl. No.: 596,514

[22] Filed: Apr. 4, 1984

[51] Int. Cl.$^4$ ............................................. A61F 13/00
[52] U.S. Cl. ................................................. 128/156
[58] Field of Search ........................ 128/155, 156, 149

[56] References Cited

U.S. PATENT DOCUMENTS

| | | |
|---|---|---|
| 3,648,692 | 3/1972 | Wheeler . |
| 3,870,041 | 3/1975 | Davies . |
| 3,890,974 | 6/1975 | Kozak . |
| 4,181,127 | 1/1980 | Linsky et al. ........................ 128/149 |
| 4,214,582 | 7/1980 | Patel . |
| 4,306,551 | 12/1981 | Hymes et al. . |
| 4,307,717 | 12/1981 | Hymes et al. . |
| 4,341,207 | 7/1982 | Steer et al. ........................... 128/156 |

*Primary Examiner*—John D. Yasko
*Attorney, Agent, or Firm*—Brumbaugh, Graves, Donohue & Raymond

[57] ABSTRACT

There is disclosed a bandage which permits drying of a wound or the wound exudate and yet which provides a barrier to bacteria, said bandage comprising an absorbent pad, a barrier film positioned over the surface of said pad, said barrier film being gas permeable and yet substantially impermeable to bacteria, an adhesive coated film or fabric positioned over and around the periphery of the pad and barrier film, said adhesive coated film or fabric being bonded to the periphery of the barrier film thus creating an open window in the center portion of the adhesive film, the adhesive coated film or fabric extending beyond the perimeter of the barrier film and said pad such that when the bandage is applied to the skin of a patient, the portion of the adhesive coated film or fabric extending beyond the perimeter of the pad and barrier film will contact the skin of the patient and form a means of attachment to the skin, the adhesive coated film or fabric and barrier film together forming a bacteria impermeable barrier. This bandage may also include a slit perforated, gas permeable, elastic film as the wound interface in order to ensure that the bandage can be removed without disrupting the wound and to minimize the pain of the injury.

9 Claims, 2 Drawing Figures

WOUND DRESSING

BACKGROUND OF THE INVENTION

The present invention is directed to an improved adhesive bandage construction. Such bandage constructions are normally used to cover and protect cuts and scrapes, particularly cuts and scrapes requiring treatment by a physician or nurse in a hospital emergency room or physician's office and follow-up treatment on an outpatient basis.

Under these circumstances, it is important to keep the injury free of contamination even though the patient returns to normal activity. Furthermore, it is frequently important to allow the injury and the wound exudate to dry out rapidly and keep it dry in order to maintain a natural barrier to external contamination of the wound. There are no assembled bandage constructions now available which provide this combination of properties. Some of the available bandages allow the exudate to dry out rapidly but these do not provide protection when bathing. Others may keep the wound clean by covering the wound with a continuous adhesive elastic film, but these do not allow the exudate to dry out rapidly. In fact, with these bandages, exudate accumulates excessively. Only one product, a laminate of foam and a microporous plastic film, was ever offered as a dressing that came close to providing these properties. But this product did not provide an adhesive seal to protect the edges of the wound and developed an excessive adhesion to the wound such that it was withdrawn from the market.

Also, many adhesive bandages, especially those for large wounds, are uncomfortable to wear since the pressure sensitive adhesive attachment and wound covering has very little elasticity and pulls the skin excessively when there is movement involving the injury. Since these bandages cannot stretch or move, any movement tends to pull the standard adhesive bandage along the skin and ultimately loosens the bandage.

The bandages presently available with an absorbent pad are essentially inelastic or have limited elasticity in only one direction. Even bandages using tricot knit fabric as the adhesive backing use an aggressive adhesive and do not provide a sufficient level of comfort. Consequently, removal of the bandage and the adhesive is almost always difficult and painful.

SUMMARY OF THE INVENTION

In accordance with the invention, there is provided an improved adhesive bandage construction which combines a complete barrier to external bacterial contamination with rapid absorption and drying of excess wound exudate. The bandage according to the invention is also more comfortable to wear, stays in place better, and is less painful to remove than conventional adhesive bandages.

These advantages are obtained by an adhesive bandage with a special external gas permeable barrier film and an absorbent paid under the film over the wound area. An elastic film or fabric coated with a special pressure sensitive adhesive is positioned around the perimeter of the barrier film and absorbent pad as the means of attaching the film and pad over the wound. When assembled from the proper components, such bandages will maintain a seal against external contaminants and yet permit the removal (from the wound) and drying of wound exudate. The external barrier film preferably has a water vapor transmission rate greater than 2000 gms/m$^2$/24 hrs at 80% RH gradient and 25° C. when tested by a procedure which keeps the film wet. This film also should have a high oxygen transmission rate. This film and adhesive attachment around the perimeter must maintain a seal against transmission or migration of bacteria to the absorbent pad and to the wound even when wet as during a shower.

In the preferred construction, the gas permeable barrier film is substantially as elastic as a thin rubber film. The improved ease of wound management is obtained in part by means of a special pressure sensitive adhesive which may be formed from an aqueous latex in such a way that rehydration and treatment with surfactant softens the adhesion to the skin and hair when it is necessary to remove the bandage.

According to a preferred embodiment the pain of the injury and wound disruption is lessened when the bandage is changed by covering the wound interface side of the absorbent pad with an oxygen and water permeable film. Films such as there are used now as primary wound coverings except they are applied with pressure sensitive adhesive directly on the wound. For this product films should have a water vapor transmission rate between 300 and 1000 gms/m$^2$/24 hrs at 80% RH gradient and 25° C., and should be perforated to permit removal of excess exudate from the surface of the wound. For this product adhesive coating is not applied directly to the wound. This wound interface film preferably is as soft and elastic as a thin rubber film. The perforations are typically a pattern of fine slits 0.5–3 mm long on $\frac{3}{8}''$ to $1''$ centers.

When the vapor permeable film perforated with slits is used as the wound interface of the absorbent pad, this permits removal of the excess wound exudate by the absorbent layer, while keeping the wound surface moist and soft during most of the first week after injury. This control of the wound environment reduces the pain of the injury and reduces the tendency for the injury to become stiff and painful to move.

The bandage is also provided with a standard silicone release paper cover over the pressure sensitive adhesive and wound interface surface of the absorbent pad. This silicone release paper cover is removed as the bandage is applied.

BRIEF DESCRIPTION OF THE DRAWINGS

For a better understanding of the invention, reference may be made to the following description of an exemplary embodiment taken in conjunction with the accompanying drawings, in which.

DESCRIPTION OF PREFERRED EMBODIMENT

Figure 1:
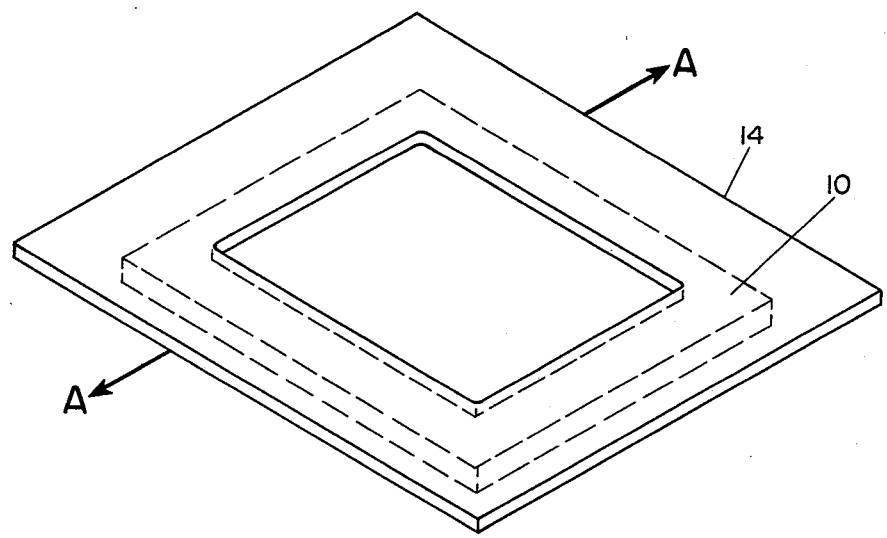
FIG. 1 is a perspective view of a bandage according to the invention.
Figure 2:
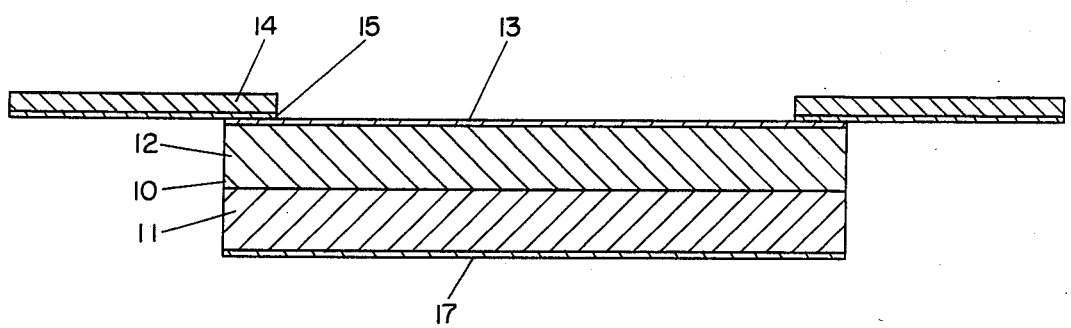
FIG. 2 is a schematic cross-sectional view of the bandage of FIG. 1 taken through line A—A of FIG. 1.

Looking to FIG. 2, there is shown an absorbent pad 10. This pad may have a single layer or may have an inner absorbent layer 11 and an outer absorbent layer 12. The absorbent pad can consist of any standard absorbent fiber web. Preferably this web should be elastic as is the case with knitted fabrics or certain nonwovens such as high loft air laid webs of rayon or cellulose fibers or multiple layers of creped cellulose wadding.

Over the pad 10 (i.e. on the side of the pad remote from the wound to be covered) there is placed the gas permeable barrier film 13. This barrier film is preferably a continuous elastic film with a very high water vapor transmission rate. Such a film can be prepared from an acrylic latex of the type used to form a soft binder for nonwoven fabrics, i.e. the acrylic polymer should be elastic and it can be prepared from a latex dispersion so as to have a high water vapor transmission rate. This is accomplished by incorporating alginate or other hydrophilic gums as thickeners for the latex. These may be crosslinked after forming the dry film (1 to 3 mils thick) by treatment with aqueous solutions of multivalent metal salts or other standard treatments. These films from acrylic elastomer latices should be manufactured so as to be pinhole-free continuous films.

Polyurethane resins are an alternative and preferred source of very permeable elastic films for this special external barrier. These may be aliphatic or aromatic and may be extruded or cast from solution or dispersion. In addition these may contain hydrophilic polymers such as polyvinyl pyrrolidone, polyvinyl prorrolidone vinyl acetate or glycol polymers to enhance their permeability. These films must also form a water resistant bond to the pressure sensitive adhesive of the elastic tape around the perimeter of the pad.

As noted above, it is preferred that the barrier film have a water vapor transmission rate greater than 2000 gms/m$^2$/24 hrs at 80% RH gradient and 25° C. It is contemplated, however, that films having lesser transmission rates (e.g. 1000 gms/m$^2$/24 hrs), while not preferred, may in some instances be employed without departing from the scope of the invention. Similarly, it is within the skill of the art to prepare films having substantially different respective transmission rates while following generally the preparation procedures set forth above.

Around the periphery of the barrier film there is bonded an elastic film or fabric 14 coated with an adhesive 15. This adhesive coated film or fabric has a hole or window in the center portion such that air and water vapor may pass through the window and also through the barrier film which underlies the entire window opening. The pressure sensitive adhesive coated film or fabric is bonded to the periphery of the barrier film 13 such that the adhesive coated film or fabric and the barrier film together form a bacterial barrier when the bandage is applied to the skin of the patient (i.e. the bond must extend around the entire perimeter of the barrier film so as to prevent bacteria from passing between the interface of the barrier film and the adhesive film).

The pressure sensitive adhesive attachment system is produced by transfer coating a pressure sensitive adhesive 15, preferably derived from an aqueous latex, to a thin elastic film or fabric such as nylon hosiery or certain spun-bonded non-wovens. If an elastic fabric is used as the carrier for the pressure sensitive adhesive then it is important to apply two layers of adhesive in order to ensure that a pinhole-free barrier is formed. As a final step in the preparation of the elastic adhesive attachment system, a window for placement of the pad is die cut from the laminate consisting of the backing film or fabric, the pressure sensitive adhesive, and silicone release paper.

According to a preferred embodiment, the bandage includes a wound interface film 17 positioned under the absorbent pad 10 and adjacent the wound. The interface film is intended to permit exudate to easily pass from the wound into the absorbent pad while maintaining a moist wound bed to minimize the pain of the injury. It is also intended to lessen the tendency of the bandage to stick to the wound, particularly during removal of the bandage.

Alternatively, the interface layer may be an open fiber web such as diaper facing fabric or a knitted fabric. Such materials permit rapid drying of the wound while still maintaining, in combination with the other bandage components, isolation of the wound from external contamination. This type of wound interface conforms to the priciples of "open" treatment of wounds without the normal risk of contamination.

The wound interface fabric for this type of "open treatment" bandage can be nearly any abrasion resistant fabric capable of transmitting wound exudate to the absorbent layer without restricting the gas transmission rate through the pad. It is preferred that this fabric also be highly elastic in both the machine and cross direction as is the case with nylon hosiery fabric or stockinette or woven fabrics which use elastic yarn in both the machine and cross direction.

For those injuries appropriately treated with new "closed" controlled environment procedures, the wound interface should be the thin highly elastic film with a water vapor transmission rate in the range of 300 to 1000 gms/m$^2$/24 hrs at 80% RH gradient as described above. This film should be continuous except for a pattern of perforations in the form of fine slits, e.g. 0.5 to 3 mm long, on approximately $\frac{1}{2}$ inch centers.

Solution cast or extruded polyurethane films, 0.6 to 2.0 mils thick, are the preferred materials for this wound interface. These may be coated with certain standard pressure sensitive adhesives for ease of perforation and lamination if the water vapor transmission rate remains within the range given above.

Controlled tests in animals have shown that partial thickness skin loss injuries covered with a bandage according to this embodiment do not adhere to the wound surface during the first few days. At the same time the wound interface is kept moist and the bandage does not disrupt the wound when removed. Telfa pads, on the other hand, become adherent to the wound through the small holes in the wound interface film and consequently removal of Telfa pads does produce fresh bleeding. An unexpected result in a similar series of animal tests was the demonstration that the bandage described herein does not adhere to or disrupt the wound surface even after being left in place for a week, during which time the thin layer of exudate on the wound surface dried to a soft flexible film. In contrast, a conventional continuous adhesive coated film applied to these wounds remains non-adherent while the accumulated wound exudate is fluid, but becomes highly adherent when this fluid dries out. Thus, removal of the conventional adhesive coated film bandage after one week from an incompletely healed injury will disrupt the wound bed and produce fresh bleeding.

Other animal tests with similar injuries contaminated with Staphlococcus aureus showed that standard topical antibacterial treatments, such as triple antibiotic ointment or silver sulfadiazine cream, could be used satisfactorily as a primary dressing under bandages according to the invention which include a wound interface film. The antibiotic ointment was quite effective when used with this controlled environment bandage.

With this absorbent pad construction, the excess exudate cannot become a source of proliferating bacteria to reinvade the wound since the exudate absorbed in the pad is dried out rapidly by evaporation through the outer barrier film which is quite permeable to water vapor. The absorbent layer may also be treated with an antibacterial agent to prevent bacterial proliferation and/or migration through the pad.

Even if the wound surface eventually dries out after a week, the surface of the injury remains flexible and the bandage can be removed easily and painlessly since the film interface does not adhere to the wound surface.

There are no adhesive bandages available which provide this last combination of properties. For example, if they are occlusive, such as bandages which cover the wound with a film of low permeability, then the initial excess exudate accumulates in a pool and can become a source of proliferating bacteria to reinvade the wound. The wound remains soft and moist and relatively comfortable for a number of days but is at risk of infection unless the wound is very clean, e.g. surgical incisions performed in an operating room. If injuries so covered are allowed to dry out, as some times occurs after one week or more, and it is necessary to remove the bandage in order to continue to apply medication to the injury, then this removal reopens the injury because the scab of dried wound exudate is attached to the pressure sensitive adhesive.

The usual approach to so-called non-adherent bandages are shown in controlled tests to be only partly non-adherent and to disrupt a significant part of the wound when removed, i.e. the pad adheres to the wound through the open holes, approximately 30% open area, in the wound interface film.

Finally, in the preferred multilayer bandage according to the present invention with a perforated film wound interface, the transparent external film will make it possible to determine whether the injury is becoming infected. Continued proliferation of bacteria in the wound produces inflammation and continued loss of fluid from the wound. This abnormal quantity of exudate will completely saturate the pad, and if this becomes apparent, the injury should be reexamined promptly by a physician. If the exudate appears in the pad only as a few small brown spots, and the injury is not sensitive to pressure, then there is no reason to expect any problem and the dressing may be left in place for as long as one week.

While the above is a description of preferred components and component properties, there are listed below specific commercially available materials which are usable in accordance with the present invention.

1. The film or fabric for the adhesive attachment around the perimeter of the pad:

A. 1.0 mil solvent cast polyurethane film (Pellethane resin from Upjohn, cast by General Foam).

B. Spun bonded polyethylene-vinyl acetate (Polyweb—60 mg/m² from James River Corporation).

C. Bleached nylon hosiery fabric (Style 82003 from Balfour Division of Kayser Roth).

2. The pressure sensitive adhesive to be applied to the above film or fabric:

A. Medical Grade Adhesive, solvent cast, 1.0 to 1.5 mil thick, Type I-679 or MF-18140, from Fasson Division of Avery International.

B. Medical Grade Adhesive, aqueous latex based, Type 9173, 1.5 mil thick, from R.P.M., Inc.

3. The bacterial barrier film used as the outer layer of the pad covering the wound:

A. A 2-mil acrylic latex film containing sodium alginate, crosslinked with calcium chloride prepared by mixing 1 part of 5% Kelcogel LV from Kelco Division of Merck and 1% glycerol with 1-parts Rhoplex E-1847 from Rohm and Haas, drying the film, treating it with 1% calcium chloride solution, and then drying again.

B. 0.6 mil solvent cast polyurethane film (Pellethane resin from Upjohn, cast by General Foam).

C. 1.2 mil solvent cast polyurethane containing 30% polyvinyl pyrollidone (Pellethane resin from Upjohn, polyvinyl pyrollidone from GAF, solvent cast by Norwood Industries).

4. The absorbent layers of the pad can be either a 1.8 oz/sq yd bonded air laid cellulose or cellulose/cotton web, e.g., Airtex from James River Corporation, or bleached cotton stockinette from the Balfour Division of Kayser Roth.

Two layers of absorbent pad material are combined with a wound interface material and the outer bacterial barrier films described above to make the complete pad. The outermost absorbent layer may be subjected to a surface treatment to inhibit bacterial migration or growth and the innermost layer is left untreated. The treatments applied to the outer absorbent layers are:

A. Citric acid buffered solution of betaine and amine oxide surfactants, C31G from E. Michaels, applied and dried, 0.2% add-on.

B. A silicone quaternary compound, Dow Corning 5700, applied as 0.1% solution in methanol, the excess wrung out and the fabric dried.

C. A substantive water repellent silicone surface applied from a dilute Ucarsil RE28 emulsion from Union Carbide with a 1% add-on of silicone polymer after drying and curing.

D. No treatment.

The wound interface will consist of an open-fabric for "open" treatment, e.g., 0.8 oz spun bond nylon (Remay from Du Pont) or bleached nylon hosiery or cotton stockinette from Balfour. For "closed" treatment, the wound interface will consist of the slit perforated membrane described above.

We claim:

1. A wound bandage comprising:
   (a) an absorbent pad having a surface facing the wound and a surface facing away from said wound when the bandage is in place on the patient;
   (b) A barrier film positioned over the surface of said pad on the surface facing away from said wound, said barrier film being gas permeable and yet substantially impermeable to bacteria;
   (c) an adhesive coated film or fabric positioned over and around the periphery of the pad and barrier film, said adhesive coated film or fabric being bonded to the periphery of the barrier film and extending beyond the perimeter of said barrier film and said pad such that when the bandage is applied to the skin of a patient, the portion of the adhesive coated film or fabric extending beyond the perimeter of the pad and barrier film will contact the skin of the patient and form a means of attachment to said skin, said adhesive coated film or fabric having an adhesive underside suitable for removably attaching the adhesive coated film or fabric to said skin;
   (d) said adhesive coated film or fabric and barrier film together forming a bacteria impermeable barrier.

2. A bandage according to claim 1 wherein said adhesive coated film or fabric is positioned over and around only the periphery of the barrier film, thus creating an open window in the center portion of the adhesive coated film or fabric and thereby facilitating the passage of gas through the center portion of the barrier film.

3. A bandage according to claim 2 wherein said barrier film has a water vapor transmission rate greater than 2000 gms/m$^2$/24 hrs at 80% RH gradient and 250° C. when tested by a procedure that keeps the film wet.

4. A bandage according to claim 3 wherein said bandage also includes an interface film on the wound interface side of the absorbent pad, said interface film being water and gas permeable so as maintain a moist wound bed for about three days.

5. A bandage according to claim 4 wherein said interface film has perforations in the form of slits, said interface film having a water vapor transmission rate between 300 and 1000 gms/m$^2$/24 hrs at 80% RH gradient and 25° C.

6. A bandage according to claim 1 wherein the barrier film is elastic.

7. A bandage according to claim 2 wherein the barrier film is elastic.

8. A bandage according to claim 6 wherein the barrier film is substantially as elastic as a thin rubber film.

9. A bandage according to claim 7 wherein the barrier film is substantially as elastic as a thin rubber film.

* * * * *